(12) United States Patent
Treat

(10) Patent No.: US 6,632,182 B1
(45) Date of Patent: Oct. 14, 2003

(54) MULTIPLE BIT, MULTIPLE SPECIMEN ENDOSCOPIC BIOPSY FORCEPS

(75) Inventor: Michael R. Treat, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/530,173

(22) PCT Filed: Oct. 23, 1998

(86) PCT No.: PCT/US98/22516
§ 371 (c)(1),
(2), (4) Date: Apr. 24, 2000

(87) PCT Pub. No.: WO99/20096
PCT Pub. Date: Apr. 29, 1999

(51) Int. Cl.[7] .................................................. A61B 10/00
(52) U.S. Cl. ..................... 600/564; 604/164.1; 606/167
(58) Field of Search ................................. 600/562–572;
604/164.1–164.12, 163; 606/205, 206, 207, 208, 209, 167, 168, 169, 170

(56) References Cited

U.S. PATENT DOCUMENTS

| 4,393,872 A | | 7/1983 | Renznik et al. |
|---|---|---|---|
| 5,256,160 A | | 10/1993 | Clement |
| 5,429,619 A | * | 7/1995 | Furnish ...................... 604/283 |
| 5,542,432 A | | 8/1996 | Slater et al. |
| 5,762,069 A | | 6/1998 | Kelleher et al. |
| 5,782,834 A | * | 7/1998 | Lucey et al. .................. 606/22 |
| 6,110,127 A | * | 8/2000 | Suzuki ....................... 600/565 |

* cited by examiner

Primary Examiner—Max Hindenburg
Assistant Examiner—Pamela L Wingood
(74) Attorney, Agent, or Firm—Reed Smith LLP

(57) ABSTRACT

A flexible or rigid endoscope biopsy device provides for the taking of multiple biopsy specimens from different sites, and for separating and storing these specimens in a partitioned container. The distal end of this device consists of a grasper which can bite or cut off a bit of tissue. The proximal end of the inner tubing is connected via the handle end of the device to a multi-chambered specimen storage device, which is itself connected to suction. The storage device has several chambers, each of which may be lined up with the inner tubing, by rotating the top of the storage device. After some or all of the storage subpartitions have been filled with specimens, the storage device can be detached from the inner tubing and handle of the device and labeled and sent directly to the pathology lab.

14 Claims, 2 Drawing Sheets

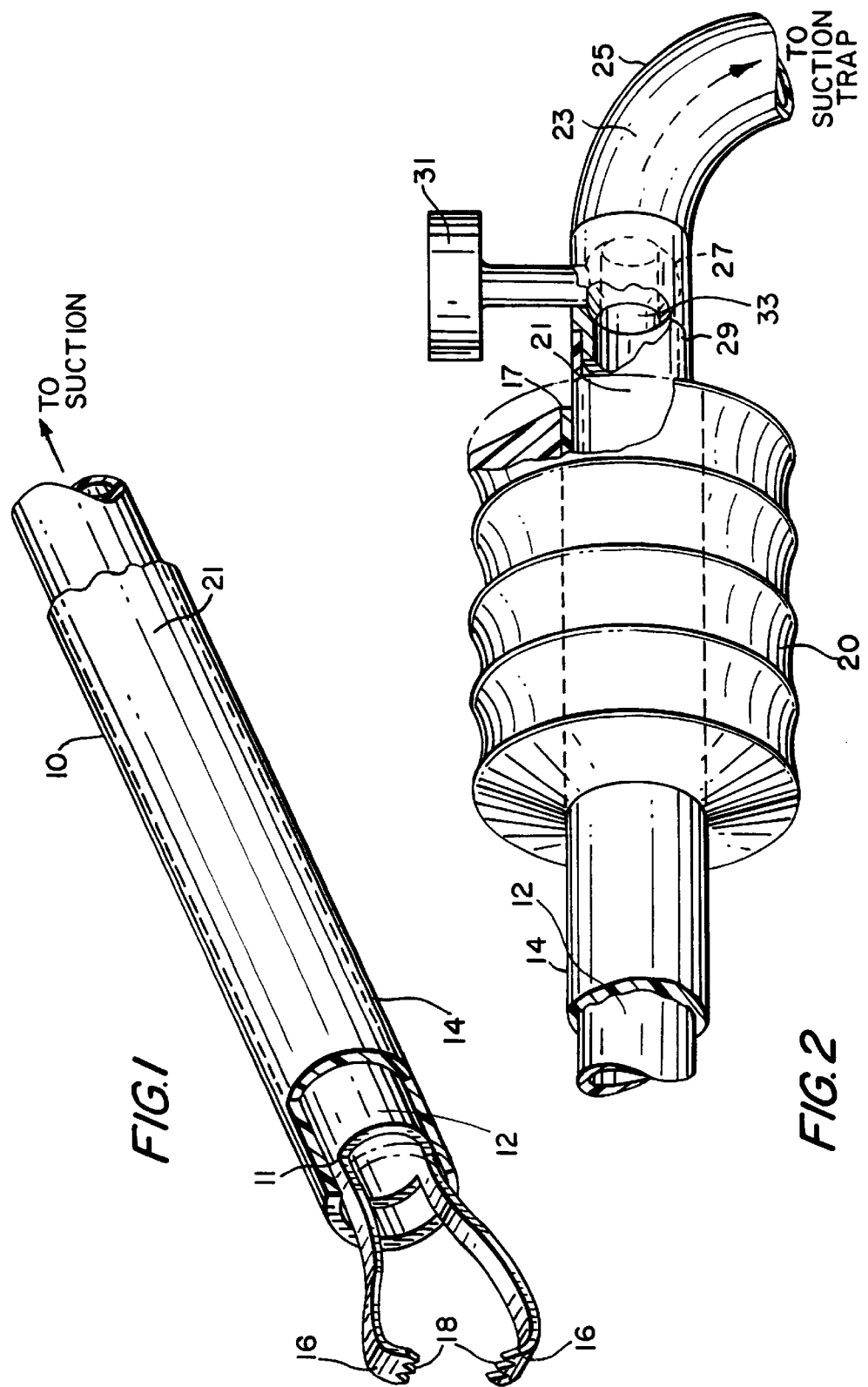

MULTIPLE BIT, MULTIPLE SPECIMEN ENDOSCOPIC BIOPSY FORCEPS

CROSS REFERENCE TO RELATED APPLICATIONS

This application is a U.S. National Phase filing of PCT Patent Application No. PCT/US98/22516, filed Oct. 23, 1998, which is based upon U.S. Provisional Patent Application Ser. No. 60/063,008, filed Oct. 23, 1997.

FIELD OF THE INVENTION

The invention relates to the field of endoscopic biopsy devices for use in obtaining samples of tissue. More particularly, this invention relates to the field of endoscopic biopsy devices, both flexible and rigid, for use in obtaining multiple samples of tissue without the need for withdrawal and reinsertion of the device during the procedure.

BACKGROUND OF THE INVENTION

An endoscope is a long, narrow instrument which is provided with a means of visualization of the tissue, and also with a means of obtaining tissue biopsy or other manipulations of tissue. The endoscope may be flexible or rigid. The means of visualization may be fiberoptic imaging or by means of a small video chip which is mounted in the distal end of the endoscope. The means of obtaining the biopsy specimen is via a long narrow channel (the "instrument channel" or "biopsy channel") which is within the body of the endoscope. Through this instrument channel a biopsy forceps is passed, which forceps is a long and narrow instrument that can fit through the channel and which has jaws or another cutting or tearing device at its distal end. The jaws device can be actuated by a lever or trigger at the proximal end (the handle) of the biopsy device.

The biopsy forceps itself can be rigid in the case of rigid endoscopes or flexible in the case of flexible endoscopes. A typical example of a flexible endoscope would be a colonoscope for examining the colon, a gastroscope for examining the stomach and upper intestine and a bronchoscope for examining the pulmonary bronchi. A typical diameter for the instrument channel of a colonoscope or gastroscope would be around 2.8 mm or slightly larger. For a bronchoscope, since the endoscope itself is narrower, the biopsy channel would be around 2 mm in diameter. Biopsy instruments compatible with these scopes must obviously be narrow enough to comfortably fit in the channel and must also be flexible, since these are all examples of flexible endoscopes.

The taking of multiple biopsy samples is necessary to properly evaluate a patient's condition in many diagnostic situations. With most current endoscopic biopsy forceps, the forceps must be withdrawn after each single bite of tissue, the jaws of the forceps must be opened and then the specimen is extracted by the nurse or endoscopic technician. To withdraw the biopsy forceps takes some time, especially in the case of a long scope (about 3 feet) such as a colonoscope, and as the forceps is being withdrawn, there is a good chance of the personnel being splashed or sprayed with bodily fluids from the patient. In the case of obtaining multiple biopsy specimens, this repeated withdrawal, extraction of a specimen from the jaws, and re-insertion of the forceps is tedious and messy.

Recently, there have appeared in limited use endoscopic biopsy forceps which can bite and hold several tissue specimens. These devices store the individual biopsy specimens in a queue which is within the jaws or just proximal to the jaws in the distal end of the instrument. Although this technology allows one to take multiple biopsies without withdrawing the instrument until the end of the series of biopsies, the individual specimen pieces in the queue must be manually separated by the nurse or technician. Since these are very tiny and irregularly shaped and sized bits, one does not always get a nice neat queue, and what one gets at the end of the instrument may look more like a "clump" of bits of tissue. It may be tedious and difficult to actually separate the pieces without confusion. A needle is usually what is used to tease out the separate pieces from the clump. Also, this process is somewhat unaesthetic and messy to perform. After the separation is done, the nurse or technician must transfer each individual bit to a separate specimen container which must be separately labelled. When one is dealing with multiple specimens, keeping all of these separate and organized and properly labelled is difficult, particularly under the time constraints of a busy endoscopy unit.

OBJECTS OF THE INVENTION

It is an object of the invention to provide an endoscopic multiple sample biopsy forceps.

It is also an object of the invention to provide a method of end-on biting or cutting to obtain multiple samples.

It is a further object of the invention to provide for a device which can retrieve multiple samples without having to withdraw the forceps between bites or cuts.

It is a yet further object of the invention to provide for such a device which can deliver the individual bits of tissue into a multi-chambered storage container which will keep the specimens separated and which will obviate the need for manual separation and handling of the specimens.

These and other objects of the invention will become more apparent from the discussion below.

SUMMARY OF THE INVENTION

This invention provides a means of overcoming the problems and disadvantages of previous multiple sample biopsy devices. With the device of the invention one can obtain multiple biopsies with a single placement of the forceps within the instrument channel of the endoscope. Also, the specimen bits are automatically separated into individual compartments of the multi-chambered specimen storage container. These compartments may be easily Labelled as to anatomic site (i.e., cecum, transverse colon, descending colon, etc.) ahead of time by stick-on labels or by use of a marking pen. Very importantly, no one in the endoscopy unit itself has to try to handle or separate out individual tiny bits of tissue which may contain infectious human bodily fluids.

Also, unlike the devices which queue the specimens in the distal end of the forceps, there is no fixed limit to the number of samples which the device of the invention can take, since one can change the multi-chambered specimen storage revolver in the handle for a new one and continue taking more samples.

In accord with the above objects of the invention, which will be discussed in more detail below, the endoscopic biopsy forceps of the present invention consists of a long, narrow, flexible or rigid, inner tubular member or tube to which are attached at the distal end, or molded integrally onto the distal end, serrated or cutting jaws. The inner lumen of this inner tubular member is such that the bits of tissue cut by the jaws can be suctioned to the proximal end of this tube. The proximal end of this tubular member is connected via an actuator such as a trumpet valve to the rotatable, revolver-type, multi-chambered specimen trap. The revolver specimen trap is attached to the actuator in such a way that each one of its separate chambers can singly or individually be connected to the proximal orifice of the actuator. The other end of the revolver specimen holder is connected to a suction source such as wall suction. There is a sieve-like floor for each of the chambers of the revolver, so that the suction can act to pull the specimen bit through the inner tube into a chamber of the trap, but the sieve material prevents the specimen from going out through the suction tubing and being lost.

The jaws of the inner tubular member are actuated by pushing an outer tubing or sheath distally to close or compress the jaws together, producing the biting or cutting action. Other biting or cutting arrangements may be used as well. See, for example, the grasping/biting/cutting configurations disclosed in U.S. Pat. Nos. 5,601,585, 5,524,634, 5,636,639, 5,638,827, 5,645,075, 5,647,115, and 5,746,216, all of which are incorporated herein by reference.

Thus, the device of the present invention permits the taking of biopsies via an endoscope in such a way that:

(1) Multiple biopsies can be obtained without withdrawal and reinsertion of the device into the endoscope. With conventional forceps, the forceps must be withdrawn after each biopsy to remove the tissue from the jaws of the forceps. Withdrawal of the forceps after each biopsy is time-consuming and also exposes the staff to the possibility of spray or aerosol contamination by the patient's bodily fluids.

(2) The biopsies can be kept separate and quite distinct from each other. Although there is a type of biopsy forceps which can "stack" or accumulate several pieces of tissue in the jaws of the forceps, there is no way to really keep these pieces distinct and separate from each other. Obviously, if one is taking specimens from different areas (some of which are benign and some of which may be malignant), it is highly desirable to have an unequivocal way of keeping the specimens separate.

(3) The person operating the forceps does not need to actually touch or directly handle the tissue specimens obtained, as is the case presently. With current biopsy forceps, the tissue specimens must be manually extracted from the jaws using a needle or other fine pointed tool. By use of the needle, each tissue specimen must be transferred to a separate specimen container. These tissue specimens are quite small (a square millimeter or so), and manipulating them is somewhat tedious and delicate to perform. Manipulating the tissue with a needle or another pointed instrument exposes the staff to the possibility of a puncture wound.

BRIEF DESCRIPTION OF THE DRAWINGS

FIG. 1 is a schematic representation of the distal end of the device of the invention showing a grasper/cutter;

FIG. 2 is a schematic representation of the proximal end of the device of the invention showing a finger grip and trumpet valve.

DETAILED DESCRIPTION OF THE INVENTION

Figure 3:
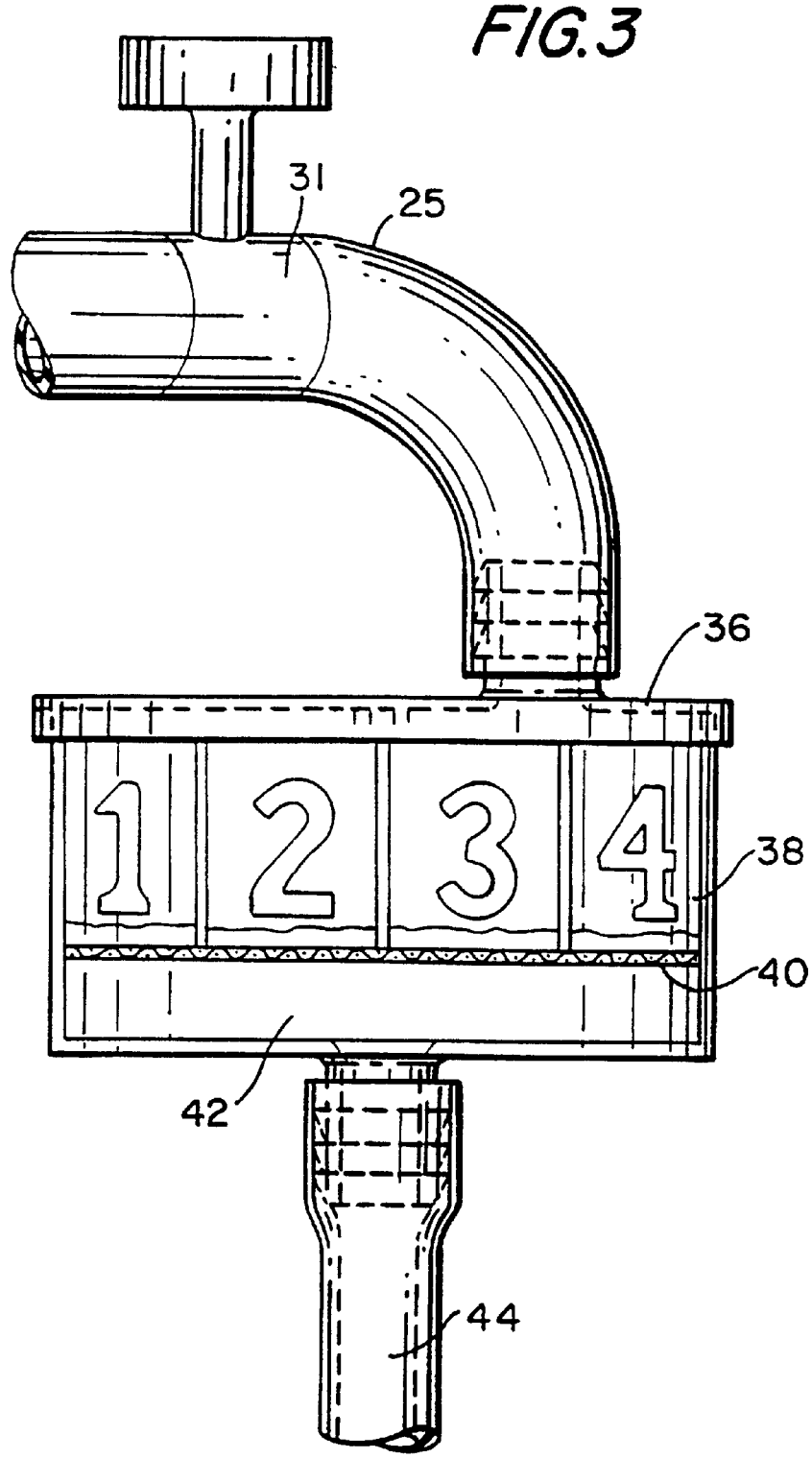
FIG. 3 is a schematic representation of suction trap mechanism attached to the proximal end of the device of the invention.

The invention can perhaps be better appreciated by referring to the drawings. With reference to FIG. 1, which depicts the distal end of the device of the invention, device 10 comprises two concentric tubular members 12,14, wherein inner tubular member 12 has attached at its distal end 11 two springy jaws 16 with serrated teeth 18. Outer tubular member 14 is slidable over inner tubular member 12. Jaws 16 are closed by pulling inner tubular member 12 into outer tubular member 14 or pushing outer tubular member 14 over jaws 16.

As mentioned above, other grasping/cutting arrangements could be useful here as well. For example, there may only be a single tubular member with the grasper at the distal end of that member. Also, a grasper such as grasper jaws can be either molded on as an integral part of the inner tubular member or attached to the inner tubular member during the manufacturing process.

In FIG. 2 the proximal end 17 of outer tubular member 14 comprises a finger grip 20. When finger grip 20 is moved distally by an operator, the distal end of outer tubular member 14 causes jaws 16 to close, thereby taking a biopsy sample.

The lumen 21 of inner tubular member 12 is in fluid communication with at least one lumen 23 of a connecting tubular member or connector 25. The distal end 27 of connector 25 is sealingly attached to the proximal end 29 of inner tubular member 12. An actuator 31, such as a trumpet valve, allows the operator to open a channel 33 between lumens 21 and 23, or within lumen 23, that causes a vacuum in lumen 21 due to a suction means in fluid communication with lumen 23.

As shown in FIG. 3 connector 25 is connected to a multi-chambered chambered specimen trap 36. This multi-chambered trap 36 has several radially arranged specimen areas 38, which are configured like the bullet chambers of a revolver. The bottom 40 of each area 38 comprises a sieve-type material. The sieve bottoms 40 of the specimen areas 38 allow the suction to pull a biopsy tissue sample into specimen trap 36 through channel 33 via tubular members 12, 25, while preventing the tissue sample from getting lost in the suction. The lower portion 42 of trap 36 is in fluid connection with additional tubing 44 that is in fluid communication with a suction or vacuum-inducing apparatus or fixture (not shown).

Specimen trap 36 is preferably configured so that only one specimen area will be exposed at a time. Then, by rotation of multi-chambered specimen trap 36, each of the individual specimen areas 38 can be brought in-line with connector 25. In this way, biopsy specimens are kept separate from each other in the separate specimen areas 38. Preferably each specimen area 38 will have a separate number or other identifying indicia imprinted thereupon.

After all the biopsy specimens have been collected, the multi-chambered trap 36 is disconnected from tubular members 25 and 44, capped and send directly to a pathology lab. The operator does not have to handle the tissue directly. If more biopsies are needed than there are chambers in a trap, then another chambered trap 36 can be attached to the end of tube 12 and used to gather additional samples.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A multiple specimen endoscopic biopsy forceps comprising:

a tubular member having proximal and distal ends and a lumen extending therethrough, and adapted to be disposed within a patient's body, a grasper extending distally from the distal end of the tubular member, whereby said grasper is disposed by the tubular member within the patient's body to be capable of providing separate specimens thereof, a connecting tubular member having proximal and distal ends and at least one lumen extending therethrough, the distal end of the connecting tubular member being sealingly attached to the proximal end of the tubular member, a specimen collector removably attached to the proximal end of the connecting tubular member to dispose the specimen collector when in use at a point exterior of the patient's body, said specimen collector having at least two chambers for collecting specimens, and a vacuum source in fluid communication with at least the connecting tubular member for establishing a vacuum within the tubular member whereby one or more of the separate specimens may be transported from the distal end of the tubular member and through the tubular member and the connecting tubular member to the specimen collector.

2. The biopsy forceps of claim 1, wherein the specimens are tissue specimens.

3. The biopsy forceps of claim 1, wherein the grasper can bite or cut off separate specimens.

4. The biopsy forceps of claim 1, wherein the grasper comprises two oppositely positioned movable jaw members.

5. The biopsy forceps of claim 1 which comprises an outer tubular member arranged concentrically around the tubular member and slidable thereover.

6. The biopsy forceps of claim 5, wherein the outer tubular member has a grip.

7. The biopsy forceps of claim 5, wherein when the outer tubular member is moved distally, it causes the grasper to close on a specimen.

8. The biopsy forceps of claim 1, wherein the connecting tubular member comprises an actuator to open or close a channel that connects the lumen of the tubular member and at least one lumen of the connector tubular member.

9. The biopsy forceps of claim 8, where the actuator is a trumpet valve.

10. The biopsy forceps of claim 1 which are flexible.

11. The biopsy forceps of claim 1 which are flexible.

12. A multiple specimen endoscopic biopsy forceps comprising:

an inner flexible tubular member having proximal and distal ends and a lumen extending therethrough, and adapted to be disposed within a patient's body, an outer tubular member concentrically arranged around said tubular member and having proximal and distal ends, a grasper extending distally from the distal end of the tubular member, whereby said grasper is disposed by the tubular member within the patient's body to be capable of separating tissue samples thereof, a connecting tubular member having proximal and distal ends and at least one lumen extending therethrough, the distal end of the connecting tubular member being sealingly attached to the proximal end of the inner tubular member, the proximal end of the outer tubular member extending when in use to a point exterior of the human body, whereby the outer tubular member is graspable to be moved with respect to the inner tubular member to actuate the grasper, a specimen collector removably attached to the proximal end of the connecting tubular member, said specimen collector having at least two chambers for receipt of specimens, and a vacuum source in fluid communication with at least the connecting tubular member.

13. The biopsy forceps of claim 12, wherein an actuator has a channel that can be opened to put the lumen of the tubular member in fluid communication with at least one lumen of the connecting tubular member.

14. The biopsy forceps of claim 13, wherein the actuator is a trumpet valve.

* * * * *